US00PP28227P2

(12) United States Plant Patent
Kordes

(10) Patent No.: US PP28,227 P2
(45) Date of Patent: Aug. 1, 2017

(54) FLORIBUNDA ROSE PLANT NAMED 'KORTRAGOSO'

(50) Latin Name: *Rosa hybrida*
Varietal Denomination: KORtragoso

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 14/999,259

(22) Filed: Apr. 14, 2016

(51) Int. Cl.
*A01H 5/02* (2006.01)

(52) U.S. Cl.
USPC ..... Plt./143

(58) Field of Classification Search
USPC ..... Plt./143, 141, 145, 146, 150, 151
CPC ..... A01H 5/0222
See application file for complete search history.

*Primary Examiner* — Kent L Bell

(57) ABSTRACT

'KORtragoso' is a new and distinct variety of *Rosa hybrida* which is characterized by the combination of a compact and bushy growth habit, dark green and semi-glossy foliage, excellent resistance to common rose diseases, and double-type flowers borne in panicles of up to 8 blooms. The small flowers are held upright and exhibit yellow petals with a red petal edge and a light fruity fragrance. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORtragoso'.

PRIOR DISCLOSURES BY THE INVENTOR

The first public disclosure of the claimed plant was made on Sep. 20, 2015 in the inventor's mail order catalog. 'KORtragoso' was not publically available or sold prior to one year before the date of the instant application.

BACKGROUND OF THE INVENTION

Parentage: The *Rosa hybrida* variety 'KORtragoso' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant, recurrent yellow and red bicolor flowers; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORtragoso' from all other varieties known to the inventor.

'KORtragoso' is a seedling selection which resulted from the controlled pollination of an unnamed *Rosa hybrida* breeding line, the seed parent, with another unnamed *Rosa hybrida* breeding line, the pollen parent, during the summer of 2005. Both breeding lines were developed and owned by the same inventor. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2006 from the seedling beds due to its superior characteristics and asexually propagated for further evaluation. This new and distinctive rose variety was given the name 'KORtragoso'.

Asexual Reproduction: 'KORtragoso' was first asexually propagated by bud grafting in July of 2006 at the inventor's nursery in Klein Offenseth-Sparrieshoop, Germany. Subsequently, 'KORtragoso' has been successfully propagated by stem cuttings and bud grafting in Jackson County, Oreg. These initial and other subsequent propagations conducted in controlled environments demonstrate that 'KORtragoso' reproduces true to type in successive generations of asexual reproduction.

SUMMARY OF THE INVENTION

The following characteristics have been repeatedly observed and represent the distinguishing characteristics of the new *Rosa hybrida* cultivar 'KORtragoso'. These traits, in combination, distinguish 'KORtragoso' as a new and distinct cultivar.

1. *Rosa hybrida* 'KORtragoso' exhibits a compact, bushy growth habit; and
2. *Rosa hybrida* 'KORtragoso' exhibits dark green and semi-glossy foliage; and
3. *Rosa hybrida* 'KORtragoso' exhibits excellent resistance to common rose diseases; and 4. *Rosa hybrida* 'KORtragoso' exhibits yellow flowers with red petal edges, borne in clusters, held upright; and
5. *Rosa hybrida* 'KORtragoso' exhibits double flowers of small size for a floribunda rose; and.
6. *Rosa hybrida* 'KORtragoso' exhibits flowers with a light fruity fragrance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORtragoso', taken from a two year old plant.

DETAILED BOTANICAL DESCRIPTION

The following is a detailed botanical description of a new and distinct variety of *Rosa hybrida* known as 'KORtragoso', based upon observations made in October of 2015 from two year old own-root plants grown outdoors in Jackson County, Oreg. Those skilled in the art will appreciate that certain characteristics will vary with older or, conversely, with younger plants. 'KORtragoso' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORtragoso' and comparisons with other varieties of *Rosa hybrida* are provided below.

General plant description:

*Growth rate*.—Moderate.

*Growth habit*.—Compact and bushy.

*Mature dimensions*.—90 cm tall and 60 cm wide, on average, when grown as a field plant.

*Cold hardiness*.—Grown successfully in USDA Hardiness Zone 6.

*Propagation*.—Stem cuttings and bud grafting.

*Disease resistance*.—Excellent resistance to Powdery mildew (*Sphaerotheca pannosa*), blackspot (*Diplocarpon rosae*), rust (*Phragmidium* sp.), and *Botrytis* (*Botrytis cinerea*) diseases under normal growing conditions in Jackson County, Oreg.

Root system: Fibrous.

Stems:

*Stem color*.—Young stems are Yellow-Green Group 146C; mature stems are Yellow-Green Group 146B.

*Anthocyanin intonations*.—Slight intonations of Greyed-Purple Group 187C are primarily present on young stems only.

*Stem surface texture*.—Both young stems and mature stems are smooth.

*Stem dimensions*.—Typical mature stems are approximately 60 to 90 cm long and 8 mm in diameter.

*Prickles*.—Incidence — Typically 22 prickles per 10 cm of stem on young wood, and 6 prickles per 10 cm of stem on mature stems, on average. Mature size — Average length is 7 mm long. Immature prickle color — Greyed-Orange Group N167A. Mature prickle color — Greyed-Orange Group 166B. Anthocyanin intonations — None. Shape — Deeply concave. Texture — Smooth.

Leaves:

*Arrangement*.—Imparipinnate compound leaves; mature axillary leaves normally with 7 leaflets.

*Attachment*.—Petiolate.

*Dimensions*.—130 mm long and 85 mm wide.

*Abundance*.—Average; approximately 60 leaves.

*Stipules*.—Size — 15 mm long and 5 mm wide. Stipule color — Yellow-Green Group 146A. Anthocyanin intonations — Intonations of Greyed-Purple Group 185C present on the central region of the adaxial surface; occasionally present on the central region of the abaxial surface. Stipitate glands — Abundant on the abaxial surface and margins. Margins — Dentate with stipitate glands. Texture, adaxial surfaces — Glabrous. Texture, abaxial surfaces — Glabrous. Apex — Apiculate. Base — Flat; fused to the petiole.

*Petiole*.—Dimensions — 15 mm long and 2.0 mm in diameter. Petiole color, adaxial surface — Yellow-Green Group 146B. Petiole color, abaxial surface — Yellow-Green Group 146C. Anthocyanin intonations — Greyed-Purple Group 184D present on the center portion of the adaxial surface. Margins — Stipitate glands present. Prickles — One prickle is present. Stipitate glands — A limited number of stipitate glands are present on the adaxial portion of the margins and also on the abaxial surface. Surface — Glabrous. Strength — Strong.

*Rachis*.—Length — Average 20 mm. Diameter — Average 1.5 mm. Color — Yellow-Green Group 146B. Anthocyanin intonations — Intonations of Greyed-Purple Group 183C are present on the adaxial portion of the margins and at the point of leaf attachment. Margins — Occasional stipitate glands. Prickles — A few small prickles underneath. Stipitate glands — A limited number of stipitate glands are present. Surfaces — Matte.

*Leaflets*.—Dimensions — Average size of the terminal leaflet is 55 mm long and 35 mm wide. Shape — Ovate. Apex — Acute. Base — Obtuse. Margins — Finely serrated; not undulated. Luster, texture and pubescence; adaxial surface — Semi-glossy, rugose, and glabrous. Luster, texture and pubescence; abaxial surface — Matte, rugose, and glabrous. Juvenile foliage color, adaxial surface — Yellow-Green Group 146A. Juvenile foliage color, abaxial surface — Yellow-Green Group 146B. Mature foliage color, adaxial surface — Green Group 137A. Mature foliage color, abaxial surface — Yellow-Green Group 146B. Anthocyanin intonations — Intonations of Greyed-Purple Group 183A present across the entire leaf surface of juvenile foliage and stems. Venation — Reticulate. Petiolule — Dimensions — 3 mm long and 1 mm in diameter. Petiolule color, adaxial surface — Yellow-Green Group 146B. Petiolule color, abaxial surface — Yellow-Green Group 146D. Anthocyanin intonations — Intonations of Greyed-Purple Group 183C are present on the adaxial surface of the margins. Prickles — None. Texture, adaxial and abaxial surfaces — Leathery.

Inflorescence:

*Inflorescence type*.—Panicles with generally 3 to 8 flowers which are held upright.

*Blooming habit*.—Recurrent; floriferous.

*Size*.—250 mm high and 120 mm wide, on average.

*Peduncle*.—Length — 60 to 80 mm average length. Diameter — 3 to 4.5 mm average diameter. Color — Yellow-Green Group 146C. Anthocyanin intonations — Intonations of Greyed-Red Group 178C. Strength — Stony. Texture — Smooth, with a limited number of stipitate glands.

Flowering laterals: Generally 1 to 2 flowering laterals are present, each with one flower per flowering shoot.

Bud:

*Bud form*.—Short; globular.

*Size*.—Upon opening, 30 mm in length from base of receptacle to distal end of bud and 15 mm diameter at its widest point.

*Texture*.—Smooth.

*Color, as sepals first unfold*.—Red Group 46B to Red Group 53A.

*Color when one-quarter open, inner side*.—Marginal zone — Red Group 46R Middle zone — Yellow-Orange Group 14B. Basal zone — Yellow-Orange Group 14B.

*Color when one-quarter open, outer side*.—Marginal zone — Red Group 46A to 46C. Middle zone — Red Group 46A to 46C. Basal zone — Red Group 46A to 46C.

Flower:

*Pedicels*.—Surface — Fine hairs and stipitate glands are present. Length — 60 to 120 mm, on average. Diameter — 2 to 3 mm, on average. Color — Greyed-Purple Group 133A. Strength — Strong to somewhat strong. Texture — Rugose.

*Calyx*.—General — Comprised of five polysepalous sepals, with very weak foliaceous appendages occasionally present on one to two of the sepals. Diameter — 55 mm. Sepals — Color, upper surface — Yellow-Green Group 146C to 146D. Color, lower surface — Yellow-Green Group 146B. Anthocyanin intonations, upper surface — Strong intonations of Greyed Purple 183D. Anthocyanin intonations, lower surface — Strong intonations of Greyed-Purple Group 184B. Size — 25 mm long and 8 mm wide, on average. Apex — Apiculate. Base — Flat at union with receptacle. Quantity — Five; occasionally six. Upper surface — Strong pubescent. Lower surface — Pubescent, with stipitate glands. Stipitate glands — Moderate density. Margins — Fine hairs with some stipitate glands present.

*Corolla*.—General shape of corolla — Shallow cup. Shape of corolla when viewed from the side — Upon opening, upper portion — Flat. Upon opening, lower portion — Flat. Open flower, upper portion — Flattened convex. Open flower, lower portion — Flattened convex. Dimensions — Small size for a floribunda rose. At anthesis, the average flower diameter is 65 mm and the average flower height is 35 mm. Fragrance — Very light fruity fragrance. Duration — On the plant for approximately 1 to 5 days. Senesced petals drop away cleanly. Petals — Petal count — Exhibits double flowers with an average of 25 to 30 petals under normal conditions. Petal reflex — Petals are somewhat reflexed. Timing of petal reflex — Simultaneous. Petal margin — Entire; slightly undulated. Petal shape — Ovate. Apex — Obtuse. Base — Obtuse Dimensions — 20 to 25 mm long and 20 to 35 mm wide. Texture, inner and outer surfaces — Smooth. Petal color, upon opening — Outermost petals, inner surface — Marginal zone — Red Group 46A to 46B. Middle zone — Yellow-Orange Group 14A, with intonations of Red Group 46D. Basal zone — Yellow-Orange Group 14A. Outermost petals, outer surface — Marginal zone — Red Group 46B to 46C. Middle zone — Yellow-Orange Group 14B, with strong intonations of Red Group 46B and 46C. Basal zone — Yellow-Orange Group 14B. Innermost petals, inner surface — Marginal zone — Yellow-Orange Group 14A, with intonations of Red Group 44B. Middle zone — Yellow-Orange Group 14A. Basal zone — Yellow-Orange Group 14A. Innermost petals, outer surface — Marginal zone — Yellow-Orange Group 14B, with intonations of Red Group 46A. Middle zone — Yellow-Orange Group 14B. Basal zone — Yellow-Orange Group 14B. Basal petal spots, upon opening — No distinct basal petal spots. Petal color, after opening — Outermost petals, inner surface — Marginal zone — Red Group 53C. Middle zone — Red Group 43C to 43D. Basal zone — Yellow Group 3C. Outermost petals, outer surface — Marginal zone — Red Group 46C. Middle zone — Red Group 46C. Basal zone — Yellow Group 2A. Innermost petals, inner surface — Marginal zone — Red Group 37B. Middle zone — Yellow Group 9B. Basal zone — Yellow Group 9B. Innermost petals, outer surface — Marginal zone — Orange Group 26D. Middle zone — Yellow Group 10A. Basal zone — Yellow Group 10A. Basal petal spots, after opening — No distinct basal petal spots. General Tonality — On open flower, Yellow-Orange Group 16B and edged with Red Group 43B. No change in general tonality at the end of the third day; thereafter the general tonality is Red Group 46B.

*Petaloids*.—Quantity — 8 petaloids per flower, on average. Dimensions — Variable; ranging from 10 to 18 mm long and 5 to 8 mm wide. Color, inner surface — Yellow-Orange Group 14A, with intonations of Orange-Red Group 38B. Color, outer surface — Yellow-Orange Group 14B, with intonations of Orange Group 28C. Margins — Very irregular; entire to undulated to indented. Shape — Spatulate to ovate. Apex — Acute to obtuse. Base — Cuneate to attenuate. Texture, inner and outer surfaces — Smooth.

Reproductive organs:

*Stamens*.—Quantity — Approximately 65, on average; regularly arranged around the styles. Anthers — Shape — Reniform. Dimensions — 1 mm long and 0.5 mm wide, on average. Color — Yellow-Orange Group 26A. Pollen — Generally present; medium density. Color is Greyed-Orange Group N167B. Filaments — Color — Yellow-Orange Group 17A. Length — 5 mm.

*Pistils*.—Quantity — Abundant; approximately 70. Stigmas — Size — 1 mm. Location — Slightly inferior in position to anthers. Color — Greyed-Yellow Group 1B. Styles — Length — Approximately 4 mm long. Color — Yellow-Green Group 149D.

*Ovary*.—Dimensions — 5 mm long and 6 mm wide. Color — White Group 155C.

*Receptacle*.—Shape — Funnel-shaped. Dimensions — Approximately 8 mm high and 10 mm wide. Surface — Glabrous and smooth, with a limited number of stipitate glands. Color — Yellow-Green Group 147C, with intonations of Greyed-Purple Group 187B which nearly cover the entire receptacle.

Hips and seed formation: Unknown.

COMPARISONS WITH THE PARENTS

The new rose plant may be distinguished from its seed parent, a proprietary *Rosa hybrida* breeding line developed by the same inventor, by the following combination of characteristics:

1. 'KORtragoso' exhibits yellow flowers with red petal edges, whereas the seed parent exhibits yellow flowers with pink petal edges.
2. 'KORtragoso' exhibits a double flower petal count, whereas the seed parent exhibits a semi-double flower count.
3. The flowers of 'KORtragoso' are larger than those of the seed parent.

The new rose plant may be distinguished from its pollen parent, a proprietary *Rosa hybrida* breeding line developed by the same inventor, by the following combination of characteristics:

1. 'KORtragoso' exhibits yellow flowers with red petal edges, whereas the pollen parent exhibits solid yellow flowers.
2. The flowers of 'KORtragoso' are larger than those of the pollen parent.

COMPARISON WITH THE MOST SIMILAR *ROSA* CULTIVAR KNOWN TO THE INVENTOR

For a comparison, several physical characteristics of the *Rosa hybrida* variety 'KORfizzlem', a rose variety from the same inventor which is described and illustrated in U.S. Plant Pat. No. 24,195, are compared to 'KORtragoso' in Chart 1.

CHART 1

| Characteristic | 'KORtragoso' | 'KORfizzlem' |
|---|---|---|
| General tonality of flower, atanthesis. | Yellow-Orange Group 16B with petal edges Red Group 43B. | Yellow Group 13C. |
| Average petal count, at anthesis. | 25 to 30. | 5. |
| Plant habit and size. | Compact and bushy. Average plant height 90 cm and average plant width 60 cm. | Upright to bushy. Average plant height 120 cm and average plant width 80 cm. |

That which is claimed:

1. A new and distinct variety of rose plant named 'KORtragoso', as described and illustrated herein.

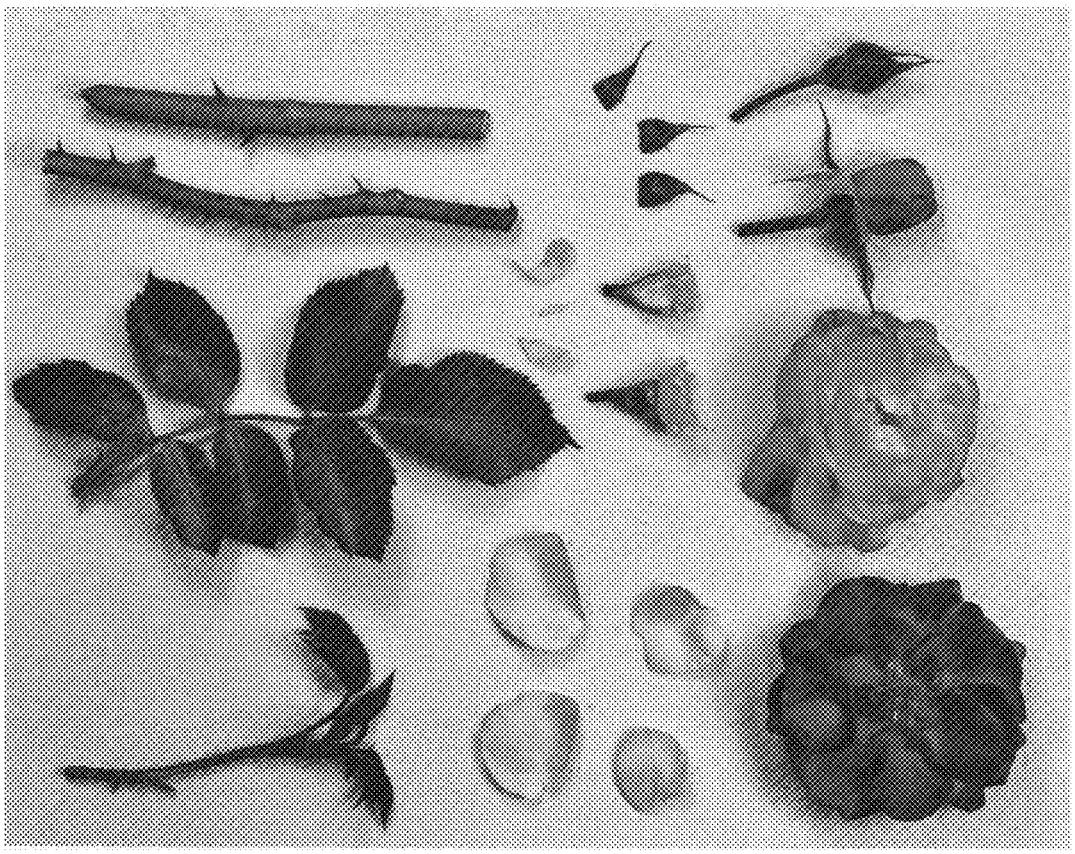

* * * * *